(12) United States Patent
Lin et al.

(10) Patent No.: US 11,065,360 B2
(45) Date of Patent: Jul. 20, 2021

(54) MEDICAL HYDROGEL COMPOSITION, AND MEDICAL HYDROGEL, PREPARATION METHOD THEREFOR AND APPLICATION THEREOF

(71) Applicant: Medprin Regenerative Medical Technologies Co., Ltd., Guangzhou (CN)

(72) Inventors: Limin Lin, Guangdong (CN); Yaya Yang, Guangdong (CN); Cheng Ma, Guangdong (CN); Kunxue Deng, Guangdong (CN); Yuyu Yuan, Guangdong (CN)

(73) Assignee: Medprin Regenerative Medical Technologies Co., Ltd., Guangdong (CN)

( * ) Notice: Subject to any disclaimer, the term of this patent is extended or adjusted under 35 U.S.C. 154(b) by 0 days.

(21) Appl. No.: 16/097,473

(22) PCT Filed: Apr. 28, 2017

(86) PCT No.: PCT/CN2017/082425
§ 371 (c)(1),
(2) Date: Oct. 29, 2018

(87) PCT Pub. No.: WO2017/186168
PCT Pub. Date: Nov. 2, 2017

(65) Prior Publication Data
US 2019/0142994 A1 May 16, 2019

(30) Foreign Application Priority Data
Apr. 29, 2016 (CN) .......................... 201610286118.4

(51) Int. Cl.
| | | |
|---|---|---|
| *A61L 24/04* | (2006.01) | |
| *A61L 24/00* | (2006.01) | |
| *A61L 31/06* | (2006.01) | |
| *A61L 27/52* | (2006.01) | |
| *A61L 27/26* | (2006.01) | |
| *A61L 31/14* | (2006.01) | |
| *A61L 27/58* | (2006.01) | |
| *A61L 31/04* | (2006.01) | |
| *A61L 27/18* | (2006.01) | |

(52) U.S. Cl.
CPC ......... *A61L 24/043* (2013.01); *A61L 24/0015* (2013.01); *A61L 24/0031* (2013.01); *A61L 27/18* (2013.01); *A61L 27/26* (2013.01); *A61L 27/52* (2013.01); *A61L 27/58* (2013.01); *A61L 31/041* (2013.01); *A61L 31/06* (2013.01); *A61L 31/145* (2013.01); *A61L 31/148* (2013.01)

(58) Field of Classification Search
CPC ........ A61L 27/18; A61L 27/58; A61L 31/148; A61L 31/145; A61L 31/041; A61L 24/0031; A61L 27/26; A61L 27/52; A61L 31/06; A61L 24/0015; A61L 24/043; C08L 71/02; C08L 79/02; C08L 77/04
See application file for complete search history.

(56) References Cited

U.S. PATENT DOCUMENTS

| | | | |
|---|---|---|---|
| 2008/0260802 A1* | 10/2008 | Sawhney | A61K 9/0014 424/426 |
| 2009/0215923 A1* | 8/2009 | Carnahan | C08L 71/02 523/118 |
| 2011/0104280 A1* | 5/2011 | Hnojewyj | A61B 17/0057 424/486 |
| 2011/0311817 A1* | 12/2011 | Kim | C07C 233/36 428/402 |
| 2012/0156259 A1* | 6/2012 | Rau | A61K 9/0024 424/400 |

FOREIGN PATENT DOCUMENTS

| | | | |
|---|---|---|---|
| CN | 102266592 A | | 12/2011 |
| CN | 102911493 A | * | 2/2013 |
| CN | 102911493 A | | 2/2013 |

OTHER PUBLICATIONS

English Translation of CN102911493 . Translated on Jul. 31, 2019. Translated from Google Patents. (Year: 2019).*

* cited by examiner

*Primary Examiner* — Doan T Phan
(74) *Attorney, Agent, or Firm* — Sheppard Mullin Richter & Hampton LLP (57) ABSTRACT

A medical hydrogel composition, a medical hydrogel, a preparation method therefore and an application thereof, and a medical hydrogel kit. The medical hydrogel composition comprises a first component and a second component; the first component comprises polylysine and polyethylene imine; the second component comprises one or more of 4-arm-polyethylene glycol-succinimidyl glutarate, 4-arm-polyethylene glycol-succinimidyl succinate, and 4-arm-polyethylene glycol-succinimidyl carbonate; the degree of polymerization of the polylysine is 20 or more. The medical hydrogel is formed by reacting the first component with the second component of the medical hydrogel composition. The medical hydrogel kit comprises the medical hydrogel composition and a buffer solution used for dissolving the components of the medical hydrogel composition. The medical hydrogel has a degree of swelling of −10%-50%, and can be applied in narrow parts where cranial, spinal, and peripheral nerves are densely distributed.

3 Claims, 6 Drawing Sheets

FIG. 11 ate, and 4-arm-polyethylene glycol-succinimidyl carbonate are all 2000 to 40000 Da, preferably 10000 to 20000 Da.

MEDICAL HYDROGEL COMPOSITION, AND MEDICAL HYDROGEL, PREPARATION METHOD THEREFOR AND APPLICATION THEREOF

CROSS-REFERENCE TO RELATED APPLICATIONS

This application is a U.S. National Stage Application under 35 U.S.C. § 371 of International Application No. PCT/CN2017/082425, filed Apr. 28, 2017, which application claims the benefit of Chinese Patent Application No. 201610286118.4, filed Apr. 29, 2016, the contents of which are hereby incorporated by reference in their entirety into the present disclosure.

TECHNICAL FIELD

The present disclosure relates to a medical hydrogel composition, a medical hydrogel, and a preparation method therefor and application thereof, and belongs to the field of biomedical technology.

BACKGROUND

Clinically, medical hydrogel may be used in the fields of in vivo wound closure, anti-adhesion, drug loading, or the like. Hydrogel is a gel using water as a dispersion medium, and has a three-dimensional network structure. It is unable to be dissolved in water, and is able to swell in water and absorb large amount of water, making the volume of the hydrogel increase. However, in narrow parts where cranial, spinal, and peripheral nerves are densely distributed, highly swellable hydrogel may cause compression to the peripheral nerves, which may interfere with the normal functions of the body, and pressure necrosis may occur in the surrounding tissues in severe cases.

Currently, most of the medical hydrogels in clinical practice, for example, Coseal mixed gel and Duraseal mixed gel, have a high degree of swelling. According to documents (Evaluation of Absorbable Surgical Sealants: In vitro Testing), these two gels have an extremely high degree of swelling. The two gels are soaked in PBS solution for three days respectively, and their weights increase by 558% and 98% correspondingly.

Patent document CN101843925A provides a low swelling hydrogel. The degree of swelling of the hydrogel is about −50% to about 50%. However, the raw material used in this patent is trilysine, which is expensive, and the obtained low swellable hydrogel is alkaline. Since most tissues are in neutral environment in human body, if an implant is alkaline, it may cause a more severe irritating effect on the surrounding cells.

SUMMARY

Technical Problem

In view of the above, the technical problem to be solved by the present disclosure is to provide a medical hydrogel composition having good biocompatibility, low degree of swelling, good biodegradability and low cost, and a medical hydrogel prepared from the medical hydrogel composition. Further, a medical hydrogel which is non-irritating to tissues is also provided.

Solution to Problem

In order to solve the above-mentioned technical problem, the present disclosure provides a medical hydrogel composition comprising a first component and a second component, the first component comprises polylysine and polyethylene imine, the second component comprises one or more of 4-arm-polyethylene glycol-succinimidyl glutarate, 4-arm-polyethylene glycol-succinimidyl succinate, and 4-arm-polyethylene glycol-succinimidyl carbonate, wherein the polylysine has a degree of polymerization of 20 or more, preferably 25 to 35.

As for the above-mentioned medical hydrogel composition, in one specific embodiment, in the first component, a mass ratio of the polylysine to the polyethylene imine is 0.1 to 10.

As for the above-mentioned medical hydrogel composition, in one specific embodiment, the polylysine is ε-polylysine and/or poly-L-lysine.

As for the above-mentioned medical hydrogel composition, in one specific embodiment, the weight average molecular weight of the ε-polylysine is 3000 to 5000 Da.

As for the above-mentioned medical hydrogel composition, in one specific embodiment, the weight average molecular weight of the poly-L-lysine is 7500 to 300000 Da, preferably 100000 to 200000 Da.

As for the above-mentioned medical hydrogel composition, in one specific embodiment, the number average molecular weight of the polyethylene imine is 1000 to 3500 Da, preferably 1500 to 2000 Da.

As for the above-mentioned medical hydrogel composition, in one specific embodiment, the weight average molecular weights of the 4-arm-polyethylene glycol-succinimidyl glutarate, the 4-arm-polyethylene glycol-succinimidyl succinate, and the 4-arm-polyethylene glycol-succinimidyl carbonate are all 2000 to 40000 Da, preferably 10000 to 20000 Da.

As for the above-mentioned medical hydrogel composition, in one specific embodiment, the medical hydrogel composition is loaded with a drug or an active factor, preferably, the first component and/or the second component contains the drug or the active factor.

The present disclosure also provides a medical hydrogel, which is formed by reacting the first component and the second component of the medical hydrogel composition of the present disclosure; preferably, the medical hydrogel is formed by reacting the first component and the second component in a buffer solution.

As for the above-mentioned medical hydrogel, in one specific embodiment, the medical hydrogel is formed as follows: dissolving the first component in a first buffer solution, dissolving the second component in a second buffer solution, and then mixing and reacting the two obtained mixtures.

As for the above-mentioned medical hydrogel, in one specific embodiment, the medical hydrogel has a degree of swelling of −10% to 50%, preferably 5% to 47%.

As for the above-mentioned medical hydrogel, in one specific embodiment, after the medical hydrogel is soaked in water, the pH value of a soaking solution is 7 to 9.5, preferably 7 to 8.

As for the above-mentioned medical hydrogel, in one specific embodiment, the pH value of the first buffer solution is 7.0 to 7.4 or 9.1 to 10.0, preferably 7.0 to 7.4; and the pH value of the second buffer solution is 5.0 to 6.0 or 7.0 to 7.4, preferably 7.0 to 7.4.

The present disclosure also provides a preparation method of the above-mentioned medical hydrogel, comprising the following steps:

dissolving the first component in the first buffer solution to obtain a first mixed solution;

dissolving the second component in the second buffer solution to obtain a second mixed solution; and mixing the first mixed solution and the second mixed solution to obtain the medical hydrogel.

As for the preparation method of the medical hydrogel, in one specific embodiment, in the first mixed solution, the concentration of the polylysine is 1 to 50 mg/mL, and the concentration of the polyethylene imine is 1 to 50 mg/mL; in the second mixed solution, the concentration of the 4-arm-polyethylene glycol-succinimidyl glutarate, the 4-arm-polyethylene glycol-succinimidyl succinate, the 4-arm-polyethylene glycol-succinimidyl carbonate, or a mixture thereof is 100 to 200 mg/mL; and the first mixed solution and the second mixed solution are mixed in an equal volume to obtain the medical hydrogel.

As for the preparation method of the above-mentioned medical hydrogel, in one specific embodiment, the second mixed solution also comprises a developer, preferably, the developer comprises one or more of FD&C Blue #1, FD&C Blue #2, and methylene blue.

The present disclosure also provides a medical hydrogel kit, which comprises the medical hydrogel composition of the present disclosure and a buffer solution for dissolving each component of the medical hydrogel composition.

As for the above-mentioned medical hydrogel kit, in one specific embodiment, the first component and the second component of the medical hydrogel composition are stored separately, preferably, the polylysine and the polyethylene imine in the first component of the medical hydrogel composition are stored separately.

The present disclosure also provides use of the above-mentioned medical hydrogel in hemostatic adjuvants, products for pulmonary air leak prevention or cerebrospinal fluid leak prevention, and anti-adhesion products.

Advantageous Effects

In the present disclosure, the prepared medical hydrogel has a low degree of swelling of only −10% to 50%, and may be applied in narrow parts where cranial, spinal, and peripheral nerves are densely distributed. The medical hydrogel prepared in the present disclosure has good biocompatibility, and good antibacterial property and biodegradability. In addition, the medical hydrogel of the present disclosure is also capable of having a non-irritating effect on tissues.

According to the following detailed description of the exemplary Examples with reference to the attached drawings, other features and aspects of the present disclosure will become clear.

BRIEF DESCRIPTION OF THE DRAWINGS

The attached drawings which are contained in the specification and constitute a part of the specification show the exemplary Examples, features and aspects of the present disclosure together with the specification, and are used to explain the principles of the present disclosure.

DETAILED DESCRIPTION

Various exemplary examples, features and aspects of the present disclosure will be described in detail below with reference to the attached drawings. The word "exemplary" used exclusively herein means "serving as an instance, an example, or illustration". Any example described herein as "exemplary" is not necessarily to be construed as preferred or superior to other examples.

In addition, in order to better illustrate the present disclosure, numerous specific details are set forth in the detailed description hereinafter. Those skilled in the art should understand that the present disclosure may also be implemented without certain specific details. In some other examples, methods, means, apparatus, and steps which are well-known to those skilled in the art are not described in detail, so as to highlight the spirit of the present disclosure.

The present disclosure provides a medical hydrogel composition and a medical hydrogel obtained by the reaction of different components of the medical hydrogel composition. The medical hydrogel composition of the present disclosure mainly comprises a first component which contains a nucleophilic reagent, and a second component which contains an electrophilic reagent. The nucleophilic reagent comprises polylysine and polyethylene imine (PEI), and the electrophilic reagent comprises one or more of 4-arm-polyethylene glycol-succinimidyl glutarate (4-arm-PEG-SG), 4-arm-polyethylene glycol-succinimidyl succinate (4-arm-PEG-SS), and 4-arm-polyethylene glycol-succinimidyl carbonate (4-arm-PEG-SC).

Of these, the first component and the second component may be separated, and the first component and the second component are mixed at the time of use. Preferably, the polylysine and the polyethylene imine (PEI) in the first component are also separated, and the polylysine and the polyethylene imine (PEI) are mixed several hours before use or at the time of use.

In the process of practical application, the polylysine and the polyethylene imine (PEI) may be each stored individually and dissolved in a same solvent before use or at the time of use. For convenience of use, the polylysine may also be stored in a form wherein it is dissolved in the solvent in advance. For example, the polylysine may be dissolved in a small amount of a buffer solution, and the mixture is diluted by using the buffer solution before use; or the polylysine may also be dissolved and stored in the buffer solution in accordance with the concentrations at which the polylysine is used. At the time of use, the polylysine dissolved in the buffer solution are mixed with the polyethylene imine (PEI). The second component is dissolved in the solvent before use or at the time of use. The present disclosure has no limitation on the storage manner of each component in the medical hydrogel composition, and those skilled in the art may select specific storage manners as needed, which are all within the scope of the present disclosure.

The polylysine of the present disclosure may be ε-polylysine and/or poly-L-lysine. The polylysine has a degree of polymerization of 20 or more, preferably between 25 and 35. In the present disclosure, the polylysine having a degree of polymerization of 20 or more, which is capable of increasing the crosslinking density and enabling the equilibrium swelling degree to decrease, is added. Of these, the weight average molecular weight of ε-polylysine is preferably 3000 to 5000 Da, and the weight average molecular weight of poly-L-lysine is 7500 to 300000 Da, preferably 100000 to 200000 Da. The number average molecular weight of the polyethylene imine (PEI) is 1000 to 3500 Da, preferably 1500 to 2000 Da.

The mass ratio of the polylysine to the polyethylene imine is 0.1 to 10.

The weight average molecular weights of the 4-arm-polyethylene glycol-succinimidyl glutarate, the 4-arm-polyethylene glycol-succinimidyl succinate, and the 4-arm-polyethylene glycol-succinimidyl carbonate contained in the second component of the medical hydrogel composition of the present disclosure are all 2000 to 40000 Da, preferably 10000 to 20000 Da.

In general, the polylysine described in the present disclosure (including ε-polylysine and poly-L-lysine) may exist in the forms of hydrochloride, hydrobromide or other salts thereof, which are all within the scope described in the present disclosure.

The medical hydrogel composition according to the present disclosure, wherein the medical hydrogel composition is loaded with a drug or an active factor. Preferably, the first component and/or the second component contain the drug or the active factor. In general, the drug may be an antibacterial agent, an anti-inflammatory drug, an anti-cancer drug, and the like, which are used for preventing/reducing the risk of infection after surgery or inhibiting the growth of cancer cells. The active factor may be a growth factor and the like, which are used for promoting tissue growth.

The manners of adding the drug and/or the active factor are as follows: the drug and/or the active factor are added to the first component and/or the second component. In general, it is preferred to add the drug to the second component. In addition, the drug may be grafted into the first component by a chemical modification method.

In another embodiment, the present disclosure also provides a medical hydrogel, which is formed as follows: dissolving the first component of the medical hydrogel composition of the present disclosure in a first buffer solution, dissolving the second component of the medical hydrogel composition is dissolved in a second buffer solution, and then mixing and reacting the two obtained mixtures.

The medical hydrogel according to the present disclosure, wherein the degree of swelling of the medical hydrogel is −10% to 50%, preferably 5% to 47%.

Specifically, the degree of swelling of the medical hydrogel described in the present disclosure refers to the change of the volume or weight between the time point when the crosslinking is effectively completed and the medical hydrogel is formed and the time point after the medical hydrogel is placed in physiological saline or a PBS solution in a free state for 24 hours (at this time point, it may be reasonably assumed that the hydrogel has achieved its equilibrium swelling state). The degree of swelling may be represented by the following formula:

degree of swelling %=[(the weight at 24 h−the weight at initial formation)/the weight at initial formation]×100%.

The first component and the second component in the medical hydrogel composition according to the present disclosure are mixed to form the medical hydrogel. When this medical hydrogel is soaked in water, the pH value of the obtained soaking solution is 7 to 9.5, preferably 7 to 8.

The acidity or basicity (pH value) of the medical hydrogel described in the present disclosure or the pH value of the soaking solution described in the present disclosure is measured by the following method: a certain amount of medical hydrogel is placed in pure water, the weight of the pure water is 80 times of that of the medical hydrogel, the medical hydrogel is placed under a constant temperature of 37° C. for 24 h, and the pH value of the soaking solution is tested.

Preferably, the pH value of the first buffer solution used to dissolve the nucleophilic reagent is 7.0 to 7.4 or 9.1 to 10.0, and the pH value of the second buffer solution used to dissolve the electrophilic reagent is 5.0 to 6.0 or 7.0 to 7.4.

The pH values of the solvents used to dissolve the nucleophilic reagent and the electrophilic reagent have a significant effect on the pH of the prepared hydrogel. When the pH value of the buffer solution used to dissolve the nucleophilic reagent is 7.0 to 7.4, the prepared medical hydrogel is nearly neutral, has little irritation to tissues, and is beneficial to the growth of cells and tissues. When the pH values of the buffer solutions used to dissolve the nucleophilic reagent and the electrophilic reagent are all 7.0 to 7.4, the prepared medical hydrogel appears to be neutral, has no irritation to tissues and cells, and is more suitable for the growth of cells and tissues.

In yet another embodiment, the present disclosure also provides a preparation method of the medical hydrogel, dissolving a first component in a first buffer solution to obtain a first mixed solution;

dissolving a second component in a second buffer solution to obtain a second mixed solution; and mixing the first mixed solution and the second mixed solution to obtain the medical hydrogel;

wherein the first component comprises polylysine and polyethylene imine, and the second component comprises one or more of 4-arm-polyethylene glycol-succinimidyl glutarate, 4-arm-polyethylene glycol-succinimidyl succinate, and 4-arm-polyethylene glycol-succinimidyl carbonate.

After the first mixed solution and the second mixed solution in the preparation method of the medical hydrogel of the present disclosure are mixed, for example, a duplex mixer may be used for mixing. Michael addition reaction of the nucleophilic reagent (the polylysine and the polyethylene imine) in the first mixed solution with the electrophilic reagent (one or more of the 4-arm-polyethylene glycol-succinimidyl glutarate, the 4-arm-polyethylene glycol-succinimidyl succinate, and the 4-arm-polyethylene glycol-succinimidyl carbonate) in the second mixed solution occurs, and the hydrogel may be formed rapidly, i.e., the medical hydrogel of the present disclosure is generated. This medical hydrogel has a good property of low swelling, and has good biocompatibility, degradability, and antibacterial effect.

Preferably, the pH value of the first buffer solution used to dissolve the nucleophilic reagent is 7.0 to 7.4 or 9.1 to 10.0, and the pH value of the second buffer solution used to dissolve the electrophilic reagent is 5.0 to 6.0 or 7.0 to 7.4. Further, when the pH value of the first buffer solution used to dissolve the nucleophilic reagent is 7.0 to 7.4, the obtained medical hydrogel appears to be neutral.

Preferably, in the first mixed solution, the concentration of the polylysine is 1 to 50 mg/mL, and the concentration of the polyethylene imine is 1 to 50 mg/mL; in the second mixed solution, the concentration of the 4-arm-polyethylene glycol-succinimidyl glutarate, the 4-arm-polyethylene glycol-succinimidyl succinate, the 4-arm-polyethylene glycol-succinimidyl carbonate, or a mixture thereof is 100 to 200 mg/mL, and the first mixed solution and the second mixed solution are mixed in an equal volume to obtain the medical hydrogel.

The preparation method of the medical hydrogel according to the present disclosure, wherein a blue developer may be further added in the second mixed solution containing the electrophilic reagent, and the alternative blue developers include FD&C Blue #1, FD&C Blue #2, methylene blue, and the like.

In yet another embodiment, the present disclosure also provides a medical hydrogel kit, which comprises the medical hydrogel composition according to the present disclosure and the first buffer solution and the second buffer solution of the present disclosure.

The medical hydrogel kit according to the present disclosure comprises a first component, a second component, a first buffer solution, and a second buffer solution. The first component comprises polylysine and polyethylene imine; and the second component comprises one or more of 4-arm-polyethylene glycol-succinimidyl glutarate, 4-arm-polyethylene glycol-succinimidyl succinate, and 4-arm-polyethylene glycol-succinimidyl carbonate, wherein the polylysine has a degree of polymerization of 20 or more, preferably 25 to 35.

The medical hydrogel kit according to the present disclosure, wherein the first component and the second component may be stored separately, and the first component and the second component are mixed at the time of use. Preferably, the polylysine and the polyethylene imine (PEI) as the nucleophilic reagent in the first component may also be stored separately, and the polylysine and the polyethylene imine (PEI) are mixed several hours before use or at the time of use.

In a specific medical hydrogel kit, the polylysine and the polyethylene imine (PEI) may be each stored individually, and are dissolved in a same solvent before use or at the time of use. For different needs of use, the polylysine may be dissolved and stored in the first buffer solution in advance, for example, the polylysine may be dissolved in a small amount of the first buffer solution and diluted before use. The polylysine may also be dissolved and stored in the first buffer solution in accordance with the concentration at which the polylysine is used. At the time of use, the polylysine dissolved in the first buffer solution is mixed with the undissolved polyethylene imine (PEI).

In addition, the second component of the present disclosure may be stored individually and dissolved in the solvent before use. The present disclosure has no limitation to the manner of storage and the manner of use of each component in the medical hydrogel kit, and suitable manner of storage and manner of use may be selected as needed.

In yet another embodiment, the medical hydrogel according to the present disclosure may be used in hemostatic adjuvants, products for pulmonary air leak prevention or cerebrospinal fluid leak prevention, anti-adhesion products, and the like, for example, applications such as blocking the suture needle holes for arteriovenous reconstruction, blocking the suture needle holes on endocranium, blocking endocranium reconstruction patch, preventing pulmonary air leak after pneumonectomy, and preventing adhesion at spinal dura mater.

EXAMPLES

The embodiments of the present disclosure would be described in detail below in conjunction with the Examples, however, those skilled in the art would understand that the following Examples were merely intended to illustrate the present disclosure and should not be considered as limiting the scope of the present disclosure. If no specific condition was noted in the Examples, the experiment was carried out in accordance with the general conditions or the conditions suggested by the manufacturers. The reagents or instruments used herein without a labeled manufacturer are all conventional products that are commercially available.

4-arm-PEG-SG (Beijing JenKem Technology Co., LTD.), 4-arm-PEG-SS (Beijing JenKem Technology Co., LTD.), 4-arm-PEG-SC (Beijing JenKem Technology Co., LTD.), ε-polylysine (Shanghai Yantuo Biotechnology Co., LTD.), poly-L-lysine (Shanghai JiNingShiye Co., LTD.), polyethylene imine (Dow Chemical (China) Co., LTD.), trilysine (Sigma Co.), and 4-arm-PEG-SH (Beijing JenKem Technology Co., LTD.).

Example 1

0.5 g of 4-arm-PEG-SG (weight average molecular weight: 15 kDa, the same shall apply hereinafter) was taken and dissolved in 5 mL of an acidic disodium hydrogen phosphate buffer solution having a pH of 5.60 to obtain a solution A having a concentration of 100 mg/mL; 20 mg of ε-polylysine (weight average molecular weight: 3500 Da, degree of polymerization: 25 to 35, the same shall apply hereinafter) and 80 mg of polyethylene imine (number average molecular weight: 1800 Da, the same shall apply hereinafter) were taken and dissolved in 5 mL of an alkaline buffer solution having a pH of 9.90 to obtain a solution B having a concentration of 20 mg/mL; and the solution A and the solution B were sprayed out in an equal dose via a duplex mixer to form a medical hydrogel I.

Example 2

0.5 g of 4-arm-PEG-SG was taken and dissolved in 5 mL of an acidic disodium hydrogen phosphate buffer solution having a pH of 5.60 to obtain a solution A having a concentration of 100 mg/mL; 50 mg of ε-polylysine and 50 mg of polyethylene imine were taken and dissolved in 5 mL of physiological saline having a pH of 7.4 to obtain a solution B having a concentration of 20 mg/mL; and the solution A and the solution B were sprayed out in an equal dose via a duplex mixer to form a medical hydrogel II.

Example 3

0.75 g of 4-arm-PEG-SG was taken and dissolved in 5 mL of an acidic disodium hydrogen phosphate buffer solution having a pH of 5.60 to obtain a solution A having a concentration of 150 mg/mL, and the developer FD&C Blue #1 was added in the solution A; 100 mg of poly-L-lysine (weight average molecular weight: 150 kDa, the same shall apply hereinafter) and 25 mg of polyethylene imine were taken and dissolved in 5 mL of physiological saline having a pH of 7.4 to obtain a solution B having a concentration of 25 mg/mL; and the solution A and the solution B were sprayed out in an equal dose via a duplex mixer to form a medical hydrogel III.

Example 4

0.5 g of 4-arm-PEG-SG was taken and dissolved in 2.5 mL of physiological saline having a pH of 7.4 to obtain a solution A having a concentration of 200 mg/mL, and the developer FD&C Blue #1 was added in the solution A; 10 mg of ε-polylysine and 90 mg of polyethylene imine were taken and dissolved in 2.5 mL of physiological saline having a pH of 7.4 to obtain a solution B having a concentration of 40 mg/mL; and the solution A and the solution B were sprayed out in an equal dose via a duplex mixer to form a medical hydrogel IV.

Example 5

0.25 g of 4-arm-PEG-SS (weight average molecular weight: 15 kDa, the same shall apply hereinafter) was taken and dissolved in 2.5 mL of physiological saline having a pH of 7.4 to obtain a solution A having a concentration of 100 mg/mL, and the developer FD&C Blue #1 was added in the solution A; 5 mg of ε-polylysine and 45 mg of polyethylene imine were taken and dissolved in 2.5 mL of physiological saline having a pH of 7.4 to obtain a solution B having a concentration of 20 mg/mL; and the solution A and the solution B were sprayed out in an equal dose via a duplex mixer to form a medical hydrogel V.

Example 6

0.25 g of 4-arm-PEG-SS and 0.25 g of 4-arm-PEG-SC (weight average molecular weight: 15 kDa, the same shall apply hereinafter) were taken and dissolved in 2.5 mL of an acidic disodium hydrogen phosphate buffer solution having a pH of 5.60 to obtain a solution A having a concentration of 200 mg/mL, and the developer FD&C Blue #1 was added in the solution A; 100 mg of poly-L-lysine and 25 mg of polyethylene imine were taken and dissolved in 2.5 mL of physiological saline having a pH of 7.4 to obtain a solution B having a concentration of 50 mg/mL; and the solution A and the solution B were sprayed out in an equal dose via a duplex mixer to form a medical hydrogel VI.

Example 7

0.5 g of 4-arm-PEG-SC was taken and dissolved in 5.0 mL of physiological saline having a pH of 7.4 to obtain a solution A having a concentration of 100 mg/mL, and the developer FD&C Blue #1 was added in the solution A; 60 mg of ε-polylysine and 90 mg of polyethylene imine were taken and dissolved in 5.0 mL of physiological saline having a pH of 7.4 to obtain a solution B having a concentration of 30 mg/mL; and the solution A and the solution B were sprayed out in an equal dose via a duplex mixer to form a medical hydrogel VII.

Comparative Example 1

0.5 g of 4-arm-PEG-SH (weight average molecular weight: 15 kDa) was taken and dissolved in 2.5 mL of a sodium dihydrogen phosphate buffer solution having a pH of 6.0 to obtain a solution A having a concentration of 200 mg/mL; 0.5 g of 4-arm-PEG-SG was taken and dissolved in 2.5 mL of a disodium hydrogen phosphate-sodium carbonate buffer solution having a pH of 9.6 to obtain a solution B having a concentration of 200 mg/mL; and the solution A and the solution B were sprayed out in an equal dose via a duplex mixer to form a medical hydrogel VIII.

Comparative Example 2

A purchased Duraseal syringe (the syringe was a duplex syringe, which comprised a nucleophilic reagent and a buffer solution 1 used to dissolve the nucleophilic reagent, and an electrophilic reagent and a buffer solution 2 used to dissolve the electrophilic reagent. Specifically, the nucleophilic reagent was trilysine, and the buffer solution 1 was a borate buffer solution having a pH of about 10, the electrophilic reagent was 4-arm-PEG-SG, and the buffer solution 2 was a phosphate buffer solution having a pH of about 4.5) was used. The nucleophilic reagent dissolved in the buffer solution 1 and the electrophilic reagent dissolved in the buffer solution 2 were sprayed out in an equal dose via a duplex mixer to form a medical hydrogel IX.

Comparative Example 3

0.5 g of 4-arm-PEG-SG was taken and dissolved in 2.5 mL of physiological saline having a pH of 7.4 to obtain a solution A having a concentration of 200 mg/mL; 0.1 g of polyethylene imine was taken and dissolved in 2.5 mL of physiological saline having a pH of 7.4 to obtain a solution B having a concentration of 40 mg/mL; and the solution A and the solution B were sprayed out in an equal dose via a duplex mixer to form a medical hydrogel X.

Comparative Example 4

0.5 g of 4-arm-PEG-SG was taken and dissolved in 2.5 mL of a sodium dihydrogen phosphate buffer solution having a pH of 6.0 to obtain a solution A having a concentration of 200 mg/mL; 0.1 g of ε-polylysine was taken and dissolved in 2.5 mL of a disodium hydrogen phosphate-sodium carbonate buffer solution having a pH of 9.6 to obtain a solution B having a concentration of 40 mg/mL. The solution A and the solution B were sprayed out in an equal dose via a duplex mixer to form a medical hydrogel XI.

The degrees of swelling of the medical hydrogels I to VII prepared in Examples 1 to 7 and the medical hydrogels VIII to IX prepared in Comparative examples 1 to 2 were measured. The above-mentioned medical hydrogels were soaked in pure water, and the pH values of the obtained soaking solutions were measured. The results were as shown in the following Table 1:

TABLE 1

| Test subject | Degree of swelling | pH value |
| --- | --- | --- |
| Example 1 | 21.61% | 9.10 |
| Example 2 | 18.04% | 7.31 |
| Example 3 | 7.37% | 7.44 |
| Example 4 | 43.34% | 7.02 |
| Example 5 | 37.92% | 7.15 |
| Example 6 | 12.56% | 7.30 |
| Example 7 | 40.68% | 7.21 |
| Comparative example 1 | 129.05% | 8.64 |
| Comparative example 2 | 198.30% | 8.55 |

As could be seen from the above-mentioned results, the degrees of swelling of the medical hydrogels I to VII prepared in Examples 1 to 7 of the present disclosure were far below those of the medical hydrogels VIII to IX prepared in Comparative examples 1 to 2. In Examples 1 to 7, the crosslinking density increased, and the degree of swelling were lower as compared with Comparative examples 1 to 2.

In Example 1 and Comparative examples 1 to 2, the solvents used to dissolve the electrophilic reagent and the nucleophilic reagent were an acidic solution and an alkaline solution, respectively, and the soaking solutions of the corresponding medical hydrogels were all alkaline. In Examples 2 to 7, the buffer solutions used to dissolve the nucleophilic reagent were neutral, and the soaking solutions of the prepared medical hydrogels were neutral. The above-mentioned results indicated that when the solvent used to dissolve the nucleophilic reagent was neutral, the soaking solution of the prepared medical hydrogel was neutral and closer to the physiological environment of human body. Therefore, the medical hydrogel prepared under this condition was safer at the time of use.

Cytotoxicity Experiment

According to the standard GB/T16886.5-2005, the toxic effects of the medical hydrogels prepared in Example 1 and Example 4 on cells in vitro were evaluated by contacting and culturing cells with the leaching liquor and observing the morphology and proliferation of cells.

The specific process of the experiment was as follows: experimental group: the medical hydrogel was leached with a serum-containing medium at a ratio of 0.1 g/mL, the obtained leaching liquor was defined as a leaching liquor having a concentration of 100%; the leaching liquor having a concentration of 100% was diluted stepwise with the serum-containing medium, the stepwise concentration gradient after dilution was 100%, 50% and 25%, and leaching liquors with said stepwise concentration gradient were used to culture cells; control group: only serum-containing medium was used, and the rest of the cell culture conditions were the same as the experimental group. The medical hydrogel I of Example 1 and the medical hydrogel IV of Example 4 were used to prepare the leaching liquor, respectively. The leaching temperature was (37±1) ° C., and the leaching time was (24±2) h. Cell culture conditions: cells were cultured in a sterile carbon dioxide incubator at 37° C.

Figure 1:
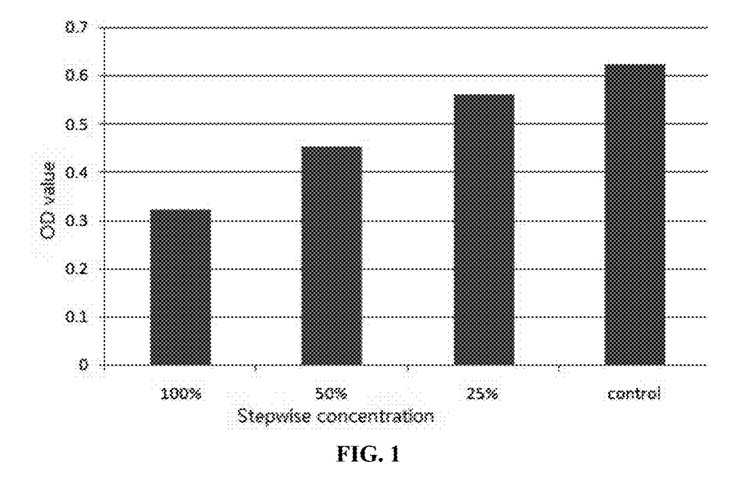
FIG. 1 shows the growth state of cells cultured in a leaching liquor of the medical hydrogel I of Example 1 for 24 h.
Figure 2:
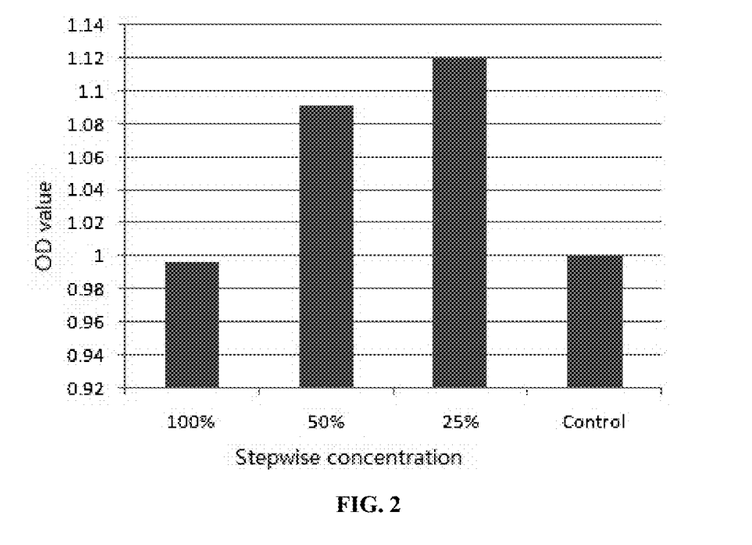
FIG. 2 shows the growth state of cells cultured in a leaching liquor of the medical hydrogel IV of Example 4 for 24 h.

FIG. 1 showed the growth state of the cells cultured in the leaching liquor of the medical hydrogel I of Example 1 for 24 h. FIG. 2 showed the growth state of the cells cultured in the leaching liquor of the medical hydrogel IV of Example 4 for 24 h. As could be seen from FIG. 1, as compared with the control group, the leaching liquor of the medical hydrogel I having a concentration of 100% had a significant effect on the growth of L929 cells. With the decrease of the concentration of the leaching liquor, the cytotoxicity tended to decrease, and the growth state of the cells was close to the growth state of the cells in the control group.

The medical hydrogel I prepared in Example 1 was alkaline, demonstrating that an alkaline leaching liquor would influence the growth of the cells to some extent.

As could be seen from FIG. 2, the growth state of the cells in the leaching liquor of the medical hydrogel IV having a concentration of 100% was close to that of the control group. With the decrease of the concentration of the leaching liquor, the cytotoxicity tended to decrease, the cell growth showed a good trend, and the growth state of the cells was superior to the growth state of the cells in the control group. The medical hydrogel IV prepared in Example 4 was neutral, thus indicating that a leaching liquor with a neutral pH did not have any hindering effect to the growth of L929 cells, and the neutral medical hydrogel was safer when used in human body.

Evaluation Experiment of Antibacterial Property

The evaluation experiment of antibacterial property was performed using the agar diffusion method: after the sterilized broth agar medium was taken and dissolved, about 20 mL of the resultant was poured to a plate having a diameter of 10 cm, and an agar plate was obtained when the medium was solidified. A sterilized cotton swab was used to dip in a test solution of a bacterium and was applied to the agar plate uniformly. Each agar plate was coated with one kind of test bacterium. Then, a sterile steel ring having a diameter of 10 mm was used to perforate uniformly, and 3 holes were made on each plate. After the agar in the hole was removed, the medical hydrogel or ε-polylysine was injected into the holes, and the medical hydrogel formed by solutions having the same volume or ε-polylysine was injected into each hole. After cultured under a constant temperature of 37° C. for 24 h, the plate was taken out. As could be seen from the results, on the periphery of each hole, there was a ring where no bacterium grew, that is, the bacteriostatic annulus. The experiment was repeated twice, and the effective diameter of the bacteriostatic annulus was calculated.

The effective diameter of the bacteriostatic annulus (mm)=the actual diameter of the bacteriostatic annulus (mm)–the diameter of the hole (10 mm).

Judgment of the results: in the case where the effective diameter of the bacteriostatic annulus was less than 10 mm, the bacterium was less sensitive or drug resistant; in the case where the effective diameter of the bacteriostatic annulus was between 10 mm to 15 mm, the bacterium was moderately sensitive; and in the case where the effective diameter of the bacteriostatic annulus was more than 15 mm, the bacterium was highly sensitive.

Since the normal state of ε-polylysine was powder and ε-polylysine would dissolve in water, in order to make a better comparison with the medical hydrogel of the present disclosure, as for ε-polylysine, the disc diffusion method was adopted. That is, a ε-polylysine solution having a certain concentration (40 mg/mL) was prepared, the solution was dropped on a disc having a diameter of 8 mm, dried in the air, and then the dried disc was placed in a nutrient agar plate.

The medical hydrogel IV of Example 4, the medical hydrogel V of Example 5, the medical hydrogels X to XI of Comparative examples 3 to 4, and a solution of ε-polylysine were selected to perform the antibacterial experiment. The selected species were *Staphylococcus aureus* and *Escherichia coli*, and their concentrations were about $10^6$ cfu/mL. The effective diameters of the bacteriostatic annuluses were as shown in the following Table 2:

TABLE 2

| Experimental subject | *Staphylococcus aureus*/mm | *Escherichia coli*/mm |
|---|---|---|
| Example 4 | 11.5 | 10.2 |
| Example 5 | 11.3 | 10.0 |
| Comparative example 3 | 9.2 | 9.0 |
| Comparative example 4 | 5.7 | 5.5 |
| ε-polylysine | 4.3 | 4.1 |

In Vitro and In Vivo Degradation Experiments

The medical hydrogel IV of Example 4 was adopted to perform the in vitro and in vivo degradation experiments, and the degradation of the medical hydrogel IV was observed at different time points. The method of the in vitro degradation experiment was as follows: the solution A and the solution B prepared in Example 4 were injected in an equal volume into a soft tube having a diameter of 6 mm and a height of 7 mm to prepare the hydrogel. The hydrogel was taken out and placed in a transparent glass bottle, and a PBS buffer solution having a pH value of 7.2±0.2 was added. The hydrogel was immersed completely, and the glass bottle was sealed and placed in a thermostatic incubator at 37±1° C. The hydrogel was observed one week, three weeks, and five weeks after the initiation of the experiment, and the degradation of the hydrogel was recorded. The results were as shown in Table 3.

The method of the in vivo degradation experiment was as follows: 8 healthy experimental rats were selected and randomly divided into 4 groups with 2 rats in each group. Then, the rats were anesthetized, the medical hydrogel IV of Example 4 was taken and subcutaneously implanted into the abdomen of the rats, the wounds were closed, and the rats were fed normally. Dissection was performed one week, three weeks, five weeks, and three months after the surgery (at each time point, one group was randomly selected to perform dissection), and the degradation of the medical hydrogel IV in rats was observed. The results were as shown in Table 3:

TABLE 3

| Degradation environment | Observation item | 1 w | 3 w | 5 w | 3 M |
|---|---|---|---|---|---|
| In vitro | Visible to naked eyes or not | Visible | Visible | Invisible | — |
| | Form of the hydrogel | Bulk | Film-like | — | — |
| In vivo | Visible to naked eyes or not | Visible | Visible | Invisible | Invisible |
| | Form of the hydrogel | Bulk | Irregular | — | — |
| | Residual amount | Much | Little | Minimum | None |

Note:
"—" represented that there was no data.

According to the above-mentioned methods of the in vitro degradation experiment and the in vivo degradation experiment, the medical hydrogel V of Example 5 and the medical hydrogel VII of Example 7 were taken respectively to perform the in vitro degradation experiment and the in vivo degradation experiment, and the results were consistent with the observed results of Example 4 (Table 3).

As could be seen from the experimental results, the medical hydrogel of the present disclosure was still able to maintain the morphology of the hydrogel after three weeks, the hydrogel was not visible to naked eyes after five weeks, and the hydrogel had been degraded completely after three months. Generally, it took a certain period of time for a wound to heal, and tissue adhesion and cerebrospinal fluid leak usually occurred about two weeks after the surgery. The hydrogel of the present disclosure was still able to maintain the morphology of the hydrogel substantially after three weeks, which was beneficial to promote the healing of a wound and reduce tissue adhesion and the risk of cerebrospinal fluid leak.

Comparative Experiments of In Vivo Degradation

The rats were anesthetized, the medical hydrogel IV of Example 4 and the medical hydrogel XI prepared in Comparative example 4 were taken respectively and subcutaneously implanted into the abdomen of the rats, and the wounds were closed. Dissection was performed three weeks, five weeks, and eight weeks after the surgery, and the degradation of the medical hydrogel was observed. The tissue near the medical hydrogel was taken and made into histological sections, and the biocompatibility of the medical hydrogel with the tissue was observed. Comprehensive scoring was performed according to the scoring criteria table for inflammation and necrosis as well as the scoring criteria for fibroplasia and repair. The calculation method of a comprehensive score was as follows: the comprehensive score=(total 1)×2+(total 2), wherein total 1: the total of the scores of inflammation and necrosis, and total 2: the total of the scores of fibroplasia and repair. The calculated total score was the comprehensive score, and said comprehensive score was merely limited to the total score of the area percentages around the implant.

Figure 3:
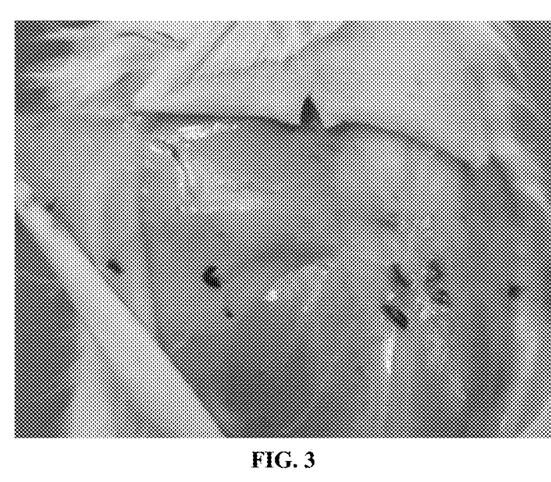
FIG. 3 shows the degradation of the medical hydrogel IV of Example 4 subcutaneously implanted in a rat at the time of dissection after five weeks.
Figure 4:
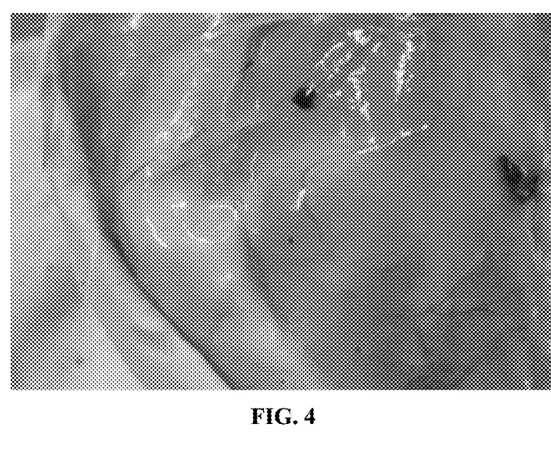
FIG. 4 shows the degradation of a medical hydrogel XI of Comparative example 4 subcutaneously implanted in a rat at the time of dissection after five weeks.

FIG. 3 showed the degradation of the medical hydrogel IV of Example 4 subcutaneously implanted in a rat at the time of dissection after five weeks. FIG. 4 showed the degradation of the medical hydrogel XI of Comparative example 4 subcutaneously implanted in a rat at the time of dissection after five weeks. As shown in FIG. 3, at the time of dissection after five weeks, there were a large number of hyperplastic capillaries at the subcutaneous implantation site in the rat, there was no subcutaneous effusion, and there was no necrosis; the medical hydrogel IV of Example 4 could not be found, and the degradation was obvious (the black granules in the figure were the suture threads). As shown in FIG. 4, at the time of dissection after five weeks, the presence of the medical hydrogel XI of Comparative example 4 could still be seen at the subcutaneous implantation site in the rat, and the degradation of the material was not obvious (the black granules in the figure were the suture threads, and the cysts portion was the undegraded hydrogel wrapped by the fibrous capsule).

Figure 5:
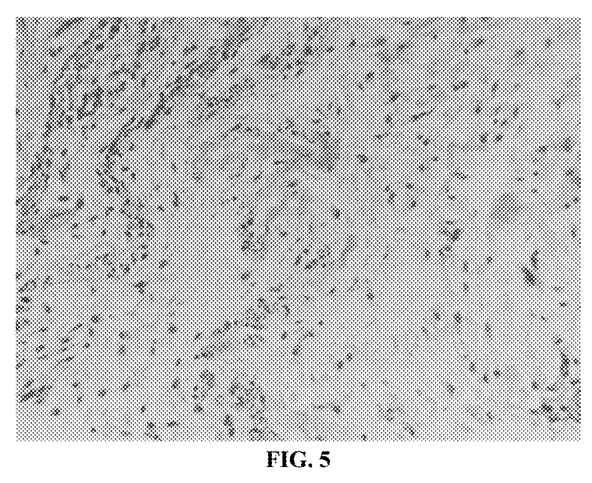
FIG. 5 shows the image of the histological section of the site where the medical hydrogel IV of Example 4 is subcutaneously implanted in a rat at the time of dissection after five weeks.

FIG. 5 showed the image (20×) of the histological section of the site where the medical hydrogel IV of Example 4 was subcutaneously implanted in a rat at the time of dissection after five weeks. As shown in FIG. 5, the implant material (the medical hydrogel IV of Example 4) was fine-granule-like. A small amount of fibroplasia could be seen around the implant material, and few lymphocytic infiltrations (1 to 5/HPF), many macrophage infiltrations (5 to 10/HPF) and plenty of capillary hyperplasia (4 to 7/HPF) could be seen. The formation of a fibrotic cyst lumen having a thin belt-like cyst lumen wall could be seen around the implant material. The scoring results of inflammation and necrosis were as shown in Table 4, the scoring results of fibroplasia and repair were as shown in Table 5, and the comprehensive score was 9.

TABLE 4

| Cell type/ | Score | | | | |
|---|---|---|---|---|---|
| Response | 0 | 1 | 2 | 3 | 4 |
| Neutrophilic granulocyte | 0 | 1 to 5/HPF* | 5 to 10/HPF | >10/HPF | The section was filled. |
| Lymphocyte | 0 | 1 to 5/HPF | 5 to 10/HPF | >10/HPF | The section was filled. |
| Plasmocyte | 0 | 1 to 5/HPF | 5 to 10/HPF | >10/HPF | The section was filled. |
| Macrophage | 0 | 1 to 5/HPF | 5 to 10/HPF | >10/HPF | The section was filled. |
| Multinuclear giant cell | 0 | 1 to 2/HPF | 3 to 5/HPF | >5/HPF | Patches of infiltration. |

TABLE 4-continued

| Cell type/ | Score | | | | |
|---|---|---|---|---|---|
| Response | 0 | 1 | 2 | 3 | 4 |
| Denaturation or necrosis | 0 | Tiny (<20%[Δ]) | Slight (21% to 40%) | Medium (41% to 70%) | Severe (>70%) |
| (Total 1) × 2 | | | 6 | | |

HPF* = high-power field (400x)
[Δ]represented the area percentage of the entire section.

TABLE 5

| | Score | | | | |
|---|---|---|---|---|---|
| Response | 0 | 1 | 2 | 3 | 4 |
| Fibroplasia | 0 | Very few capillary hyperplasia (1 to 3/HPF), focal, 1 to 3 fibroblast hyperplasia as initial nidus | 4 to 7 capillary masses (4 to 7/HPF) accompanied by fibroblast hyperplasia | Broad belt-like capillaries (8 to 20/HPF) and fibroblast hyperplasia | Extensive belt-like capillaries (>20/HPF) and fibroblast hyperplasia |
| Formation of the fibrotic cyst lumen | 0 | Thin belt-like cyst lumen wall (<10 layers) | Medium-thick belt-like (10 to 50 layers) | Thick belt-like (50 to 100 layers) | Extensive belt-like (>100 layers) |
| Fatty infiltration | 0 | Very few adipocytes accompanied by fibrosis (<20%) around the implant. | Few adipocytes and fibrotic layers (21% to 40%) around the implant. | Narrow and large range of adipocyte aggregation (41% to 70%) could be seen around the implant. | Extensive fatty infiltration (>70%) could be seen around the implant. |
| Total 2 | | | 3 | | |

Figure 6:
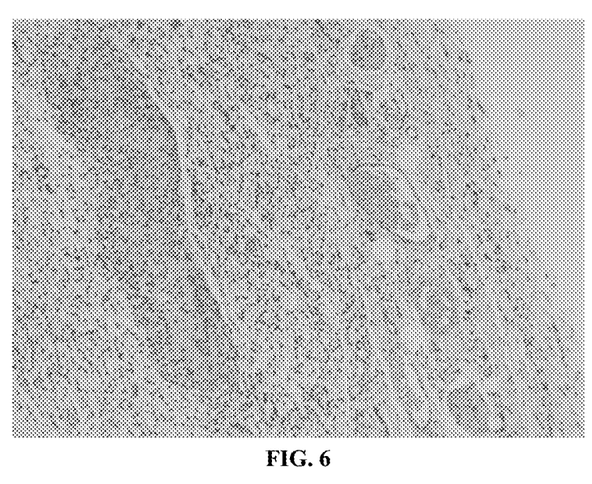
FIG. 6 shows the image of the histological section of the site where the medical hydrogel XI of Comparative example 4 is subcutaneously implanted in a rat at the time of dissection after five weeks.

FIG. 6 showed the image (20×) of the histological section of the site where the medical hydrogel XI of Comparative example 4 was subcutaneously implanted in a rat at the time of dissection after five weeks. As shown in FIG. 6, the implant material (the medical hydrogel XI of Comparative example 4) was fragmented and loose inside. It could be seen that many fibroblasts grew into the interior of the material, the area percentage of the remaining material was about 1% to 5%, and no significant gap was observed between the material and the surrounding tissues. Many fibroplasias could be seen around the implant material, and few lymphocytic infiltrations (1 to 5/HPF), many macrophage infiltrations (5 to 10/HPF), few multinuclear giant cell infiltrations (1 to 2/HPF), and plenty of capillary hyperplasia (4 to 7/HPF) could be seen. The formation of a medium-thick belt-like fibrous capsule and a large range of adipocyte infiltration (21% to 40%) could be seen around the implant material. The scoring results of inflammation and necrosis were as shown in Table 6, the scoring results of fibroplasia and repair were as shown in Table 7, and the comprehensive score of inflammation and fibroplasia was 14.

TABLE 6

| Cell type/ | Score | | | | |
|---|---|---|---|---|---|
| Response | 0 | 1 | 2 | 3 | 4 |
| Neutrophilic granulocyte | 0 | 1 to 5/HPF* | 5 to 10/HPF | >10/HPF | The section was filled. |
| Lymphocyte | 0 | 1 to 5/HPF | 5 to 10/HPF | >10/HPF | The section was filled. |
| Plasmocyte | 0 | 1 to 5/HPF | 5 to 10/HPF | >10/HPF | The section was filled. |
| Macrophage | 0 | 1 to 5/HPF | 5 to 10/HPF | >10/HPF | The section was filled. |
| Multinuclear giant cell | 0 | 1 to 2/HPF | 3-5/HPF | >5/HPF | Patches of infiltration. |
| Denaturation or necrosis | 0 | Tiny (<20%[Δ]) | Slight (21% to 40%) | Medium (41% to 70%) | Severe (>70%) |
| (Total 1) × 2 | | | 8 | | |

HPF* = high-power field (400x)
[Δ]represented the area percentage of the entire section.

TABLE 7

| | Score | | | | |
|---|---|---|---|---|---|
| Response | 0 | 1 | 2 | 3 | 4 |
| Fibroplasia | 0 | Very few capillary hyperplasia (1 to 3/HPF), focal, 1 to 3 fibroblast hyperplasia as initial nidus | 4 to 7 capillary masses (4 to 7/HPF) accompanied by fibroblast hyperplasia | Broad belt-like capillaries (8 to 20/HPF) and fibroblast hyperplasia | Extensive belt-like capillaries (>20/HPF) and fibroblast hyperplasia |
| Formation of the fibrotic cyst lumen | 0 | Thin belt-like cyst lumen wall (<10 layers) | Medium-thick belt-like (10 to 50 layers) | Thick belt-like (50 to 100 layers) | Extensive belt-like (>100 layers) |
| Fatty infiltration | 0 | Very few adipocytes accompanied by fibrosis (<20%) around the implant. | Few adipocytes and fibrotic layers (21% to 40%) around the implant. | Narrow and large range of adipocyte aggregation (41% to 70%) could be seen around the implant. | Extensive fatty infiltration (>70%) could be seen around the implant. |
| Total 2 | | | 6 | | |

As could be seen from the analysis of the above-mentioned results, the medical hydrogel IV of Example 4 had better biocompatibility with tissues, and the medical hydrogel IV of Example 4 had been subcutaneously degraded in the rat completely after eight weeks while a part of the medical hydrogel XI of Comparative example 4 was still undegraded.

As for the body, the in vivo implant, as a foreign matter, should be taken out or degraded after it achieved its certain goal. The time for post-traumatic healing was about 1 to 8 weeks for most of the surgeries in human body, therefore, the medical hydrogel IV of Example 4 was more suitable for clinical use in terms of degradation time.

Animal Experiment of Blocking Suture Needle Holes on Endocranium

A dog as an experimental animal was anesthetized, the left parietal bone of the dog as the experimental animal was incised, and a piece of skull having a size of 3 cm×2.5 cm was taken out. The left endocranium of the dog as the experimental animal was incised, and the length of the incision was 2.0 cm. The incision of the endocranium was sutured with a suture thread (4-0 nylon thread) with an interval of 2 mm to 3 mm. The medical hydrogel IV of Example 4 was injected to the sutured site. After the medical hydrogel IV was solidified, the removed skull was put back, and the skin of the wound was sutured. The dog as the experimental animal was fed for 4 weeks.

Observation indexes: (1) The following was evaluated qualitatively after the surgery: whether the behavior of the dog as the experimental animal was normal, the general health information (such as the healing of the incision, appetite, and body weight), and abnormal behaviors which were probably caused by cerebrospinal fluid leak. (2) Before the dog as the experimental animal was sacrificed, first, the intracranial pressure of the dog as the experimental animal was measured using a lumbar puncture set and the value was recorded, then, the intracranial pressure was elevated to 200 mm water column by injecting physiological saline and was kept for at least 5 seconds, and whether there was cerebrospinal fluid leak at the needle holes was observed. (3) The following was observed by naked eyes: the position of the incision of the endocranium, and the degradation and adhesion (with brain tissue) of the medical hydrogel IV.

Figure 7:
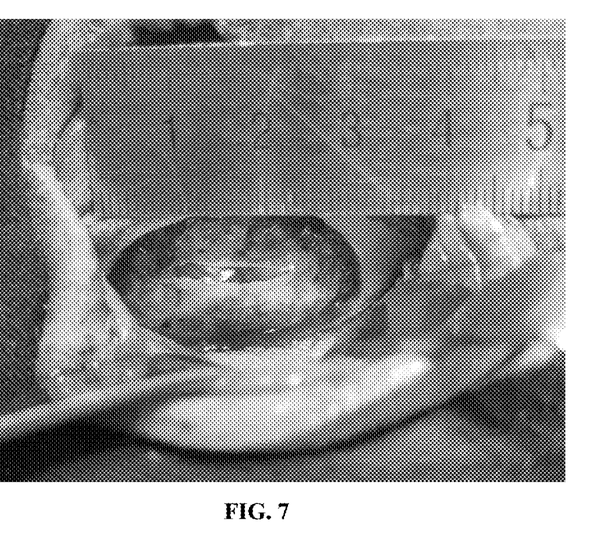
FIG. 7 shows a picture of the incised endocranium of a dog as an experimental animal.
Figure 8:
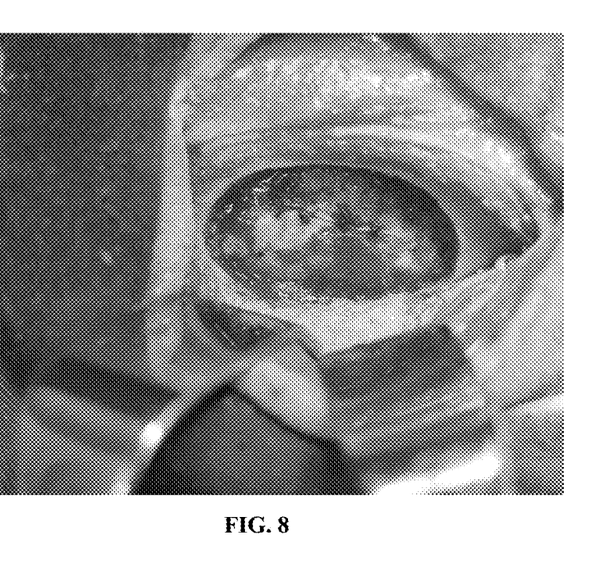
FIG. 8 shows a picture of the sutured endocranium of the dog as the experimental animal.
Figure 9:
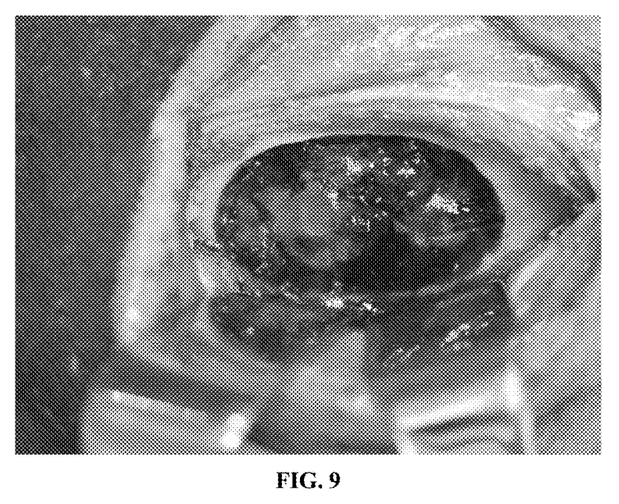
FIG. 9 shows a picture in which the medical hydrogel is injected after the endocranium of the dog as the experimental animal is sutured.
Figure 10:
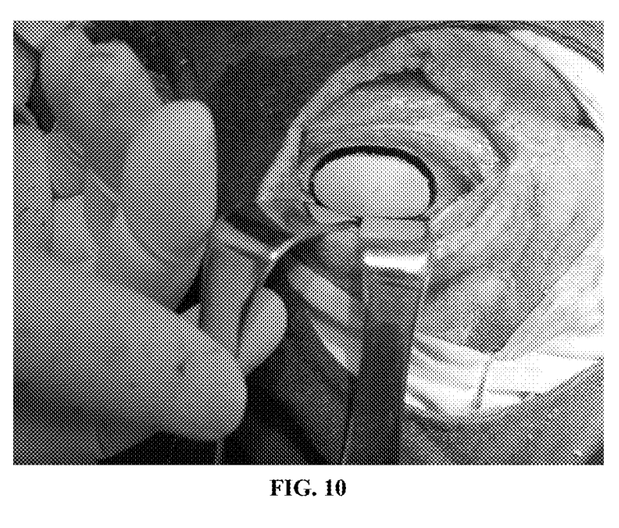
FIG. 10 shows a picture in which the endocranium of the dog as the experimental animal is put back into the skull after the hydrogel is injected.
Figure 11:
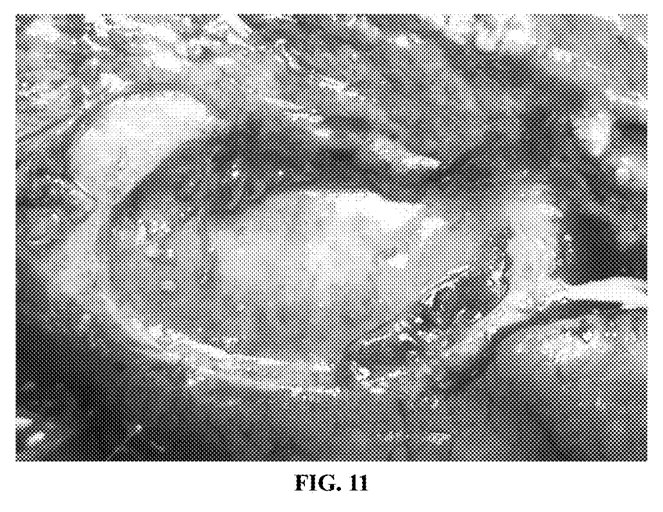
FIG. 11 shows a picture of the healing condition and the repairing effect at the incision site of the endocranium of the dog as the experimental animal after 4 weeks of feeding.

FIG. 7 showed a picture of the incised endocranium of the dog as the experimental animal. FIG. 8 showed a picture of the sutured endocranium of the dog as the experimental animal. FIG. 9 showed a picture in which the medical hydrogel was injected after the endocranium of the dog as the experimental animal was sutured. FIG. 10 showed a picture in which the endocranium of the dog as the experimental animal was put back into the skull after the hydrogel was injected. FIG. 11 showed a picture of the healing condition and the repairing effect at the incision site of the endocranium of the dog as the experimental animal after 4 weeks of feeding. As shown in FIGS. 7 to 11, 1 to 4 weeks after the surgery, the incision of the skin of the dog as the experimental animal healed as normal, there was no significant difference in terms of appetite and body weight, and the animal behaved normally. Dissection was performed 4 weeks after the surgery, and there was no adhesion between the endocranium and the upper tissues. The medical hydrogel was invisible to naked eyes. When the intracranial pressure increased to 200 mm water column, no cerebrospinal fluid leak appeared at the surgical site at 8 seconds.

As could be seen from the above-mentioned experiment, the medical hydrogel IV formed in the present disclosure has low degree of swelling, appears as neutral, and has good biocompatibility, the ability to be degraded in vivo, and antibacterial effect; and no cerebrospinal fluid leak would appear.

Those mentioned above are merely specific embodiments of the present disclosure, however, the protection scope of the present disclosure is not limited thereto, and any variation or alternative which is readily occur to those skilled in the art as within the technical scope disclosed in the present disclosure should be encompassed in the protection scope of the present disclosure. Therefore, the protection scope of the present disclosure should be subject to the protection scope of the claims.

Applicability

The medical hydrogel composition, the medical hydrogel and the preparation method and application thereof provided in the Examples of the present disclosure may be applied in the field of biomedical technology, in particular, used in hemostatic adjuvants, products for pulmonary air leak prevention or cerebrospinal fluid leak prevention, anti-adhesion products, and the like, for example, applications such as blocking the suture needle holes for arteriovenous reconstruction, blocking the suture needle holes on endocranium, blocking endocranium reconstruction patch, preventing pulmonary air leak after pneumonectomy, and preventing adhesion at spinal dura mater. The medical hydrogel prepared in the present disclosure has good biocompatibility, and has good antibacterial property and biodegradability. In addition, the medical hydrogel of the present disclosure is also capable of having a non-irritating effect on tissues.

What is claimed is:

1. A medical hydrogel kit, comprising:
a first component comprising polylysine and polyethylene imine (PEI), wherein the polylysine is ε-polylysine having an average molecular weight of 3000 to 5000 Da or poly-L-lysine having an average molecular weight of 7500 to 300000 Da, the polylysine has a degree of polymerization of 20 or more, and the polylysine and the PEI have a mass ratio of 0.1 to 1;
a second component selected from the group consisting of 4-arm-polyethylene glycol-succinimidyl glutarate, 4-arm-polyethylene glycol-succinimidyl succinate, 4-arm-polyethylene glycol-succinimidyl carbonate, and combinations thereof, wherein the second component has an average molecular weight of 10,000 to 20,000 Da; and
a saline solution,
wherein the first component, the second component and the saline solution react to form a medical hydrogel having a degree of swelling of 5% to 47% when mixed together, and
wherein the formed medical hydrogel has a complete in vivo degradation time from 5 to 8 weeks.

2. The medical hydrogel kit according to claim 1, wherein the first component and the second component are stored separately.

3. The medical hydrogel kit according to claim 1, wherein the saline solution has a pH of 7.0 to 7.4.

* * * * *